(12) United States Patent
Prior

(10) Patent No.: US 9,662,115 B2
(45) Date of Patent: May 30, 2017

(54) EEA ABDOMINAL ACCESS DEVICE

(71) Applicant: Covidien LP, Mansfield, MA (US)

(72) Inventor: Scott Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 747 days.

(21) Appl. No.: 13/975,607

(22) Filed: Aug. 26, 2013

(65) Prior Publication Data

US 2015/0053747 A1 Feb. 26, 2015

(51) Int. Cl.
| | | |
|---|---|---|
| *A61B 17/115* | (2006.01) | |
| *A61B 17/34* | (2006.01) | |
| *A61B 17/02* | (2006.01) | |
| *A61B 46/13* | (2016.01) | |
| *A61B 46/10* | (2016.01) | |
| *A61B 90/40* | (2016.01) | |

(52) U.S. Cl.
CPC ...... *A61B 17/1155* (2013.01); *A61B 17/0218* (2013.01); *A61B 17/3415* (2013.01); *A61B 17/3423* (2013.01); *A61B 17/3431* (2013.01); *A61B 46/10* (2016.02); *A61B 46/13* (2016.02); *A61B 17/0293* (2013.01); *A61B 90/40* (2016.02); *A61B 2017/0225* (2013.01); *A61B 2017/3435* (2013.01); *A61B 2017/3441* (2013.01); *A61B 2017/3452* (2013.01)

(58) Field of Classification Search
CPC ............ A61B 17/0218; A61B 17/0293; A61B 17/1155; A61B 17/3415; A61B 17/3423; A61B 17/3431; A61B 17/0225; A61B 2017/3435; A61B 2017/3441; A61B 2017/3452

USPC ....................................................... 227/179.1
See application file for complete search history.

(56) References Cited

U.S. PATENT DOCUMENTS

| | | | | |
|---|---|---|---|---|
| 4,271,839 A | * | 6/1981 | Fogarty | A61M 25/0119 604/271 |
| 4,937,881 A | * | 7/1990 | Heise | A41D 19/0075 15/227 |
| 5,020,159 A | * | 6/1991 | Hellickson | A41D 19/0075 2/158 |

(Continued)

FOREIGN PATENT DOCUMENTS

| | | |
|---|---|---|
| CA | 2805365 A1 | 8/2013 |
| EP | 2168510 A1 | 3/2010 |

(Continued)

OTHER PUBLICATIONS

Extended European Search Report from Appl. No. 14181908.6 dated May 26, 2015.

(Continued)

*Primary Examiner* — Hemant M Desai
*Assistant Examiner* — Valentin Neacsu

(57) ABSTRACT

A surgical system is disclosed, and includes a surgical fastening apparatus and an access device. The access device defines an internal lumen configured to receive the surgical fastening apparatus. The access device also includes a proximal portion and a distal portion being more flexible than the proximal portion. The access device is reconfigurable between a first condition and a different, second condition in which the distal portion of the access device is configured to fold radially inwardly and proximally upon movement of the surgical fastening apparatus therewith.

7 Claims, 4 Drawing Sheets

(56) References Cited

U.S. PATENT DOCUMENTS

| | | | |
|---|---|---|---|
| 5,752,970 A | 5/1998 | Yoon | |
| 5,842,971 A | 12/1998 | Yoon | |
| 5,853,395 A * | 12/1998 | Crook | A61B 17/3423 600/208 |
| 5,997,515 A | 12/1999 | de la Torre et al. | |
| 6,033,428 A * | 3/2000 | Sardella | A61B 17/3423 606/213 |
| 6,238,373 B1 | 5/2001 | de la Torre et al. | |
| 2001/0037053 A1 | 11/2001 | Bonadio et al. | |
| 2004/0073090 A1 | 4/2004 | Butler et al. | |
| 2004/0092795 A1 * | 5/2004 | Bonadio | A61B 17/3423 600/207 |
| 2007/0203398 A1 | 8/2007 | Bonadio et al. | |
| 2008/0010720 A1 * | 1/2008 | Weiser | A41D 19/0075 2/161.6 |
| 2008/0097162 A1 | 4/2008 | Bonadio et al. | |
| 2009/0001121 A1 * | 1/2009 | Hess | A61B 17/105 227/175.1 |
| 2009/0326465 A1 * | 12/2009 | Richard | A61B 17/3423 604/167.01 |
| 2010/0081871 A1 * | 4/2010 | Widenhouse | A61B 17/3462 600/104 |
| 2010/0249525 A1 * | 9/2010 | Shelton, IV | A61B 17/3423 600/208 |
| 2010/0261970 A1 * | 10/2010 | Shelton, IV | A61B 17/3423 600/203 |
| 2012/0130187 A1 * | 5/2012 | Okoniewski | A61B 17/3423 600/208 |
| 2012/0157777 A1 * | 6/2012 | Okoniewski | A61B 17/3423 600/201 |
| 2012/0157783 A1 | 6/2012 | Okoniewski et al. | |
| 2013/0172681 A1 * | 7/2013 | Smith | A61B 17/3423 600/203 |
| 2013/0225932 A1 * | 8/2013 | Smith | A61B 1/313 600/206 |

FOREIGN PATENT DOCUMENTS

| | | |
|---|---|---|
| JP | 2013-138860 A | 7/2013 |
| WO | 98/35614 A1 | 8/1998 |

OTHER PUBLICATIONS

European Examination Report from Appl. No. 14181908.6 dated May 3, 2016.

* cited by examiner

EEA ABDOMINAL ACCESS DEVICE

BACKGROUND

1. Technical Field

The present disclosure relates generally to a surgical fastening device for applying surgical fasteners to body tissue. More particularly, the present disclosure relates to a surgical device and access device suitable for introducing that surgical device into hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a fastener instrument which drives a circular array of fasteners, e.g., staples, through the end section of each organ section and simultaneously cores any tissue interior of the driven circular array of staples to free the tubular passage. Examples of instruments for performing circular anastomosis of hollow organs are described in U.S. Pat. Nos. 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument and a fastener holding component disposed at a distal end. An anvil assembly including an anvil rod with attached anvil head is mounted to the distal end of the instrument adjacent the fastener holding component. Opposed end portions of tissue of the hollow organ(s) to be fastened are clamped between the anvil head and the fastener holding component. The clamped tissue is joined by driving one or more fasteners from the fastener holding component so that the ends of the fasteners pass through the tissue and are deformed by the anvil head. An annular knife is concurrently advanced to core tissue of the hollow organ to free a tubular passage within the organ.

A surgical fastening device is inserted through a naturally-occurring orifice or an incision formed in e.g., the abdomen. Additionally, in many anastomosis procedures, portions of the anvil assembly and/or fastener holding component may come into contact with, e.g., diseased tissue or septic materials at a working site which are undesirable to be spread to other portions of the body.

Accordingly, it would be desirable to provide a system including a surgical device and an associated access device which simultaneously facilitates access through an incision and maintains a barrier between the site and/or hollow organ and the surgical device.

SUMMARY

A surgical system is disclosed, and includes a surgical fastening apparatus and an access device. The access device defines an internal lumen configured to receive the surgical fastening apparatus. The access device also includes a proximal portion and a distal portion being more flexible than the proximal portion. The access device is reconfigurable between a first condition and a different, second condition in which the distal portion of the access device is configured to fold radially inwardly and proximally upon movement of the surgical fastening apparatus therewith.

According to one aspect of the present disclosure, the access device defines a partially enclosed distal end. The partially enclosed distal end may include an aperture. According to another aspect of the present disclosure, the surgical fastening apparatus includes a distal head portion defining a first diameter, and the aperture defines a second, different diameter. The second diameter may be different than the first diameter. In another aspect of the present disclosure a portion of the surgical fastening apparatus is configured to frictionally engage the aperture. According to yet another aspect of the present disclosure, the proximal portion of the access device includes a flange.

According to another aspect of the present disclosure, a surgical access device is disclosed, and includes a proximal portion and a distal portion. The proximal portion is formed of a first material and defines an opening. The distal portion is formed of a different, second material, and the distal portion is movable with respect to the proximal portion and defines an aperture. The aperture is configured to frictionally engage a surgical fastening apparatus, and the distal portion is configured to invert upon proximal movement of the surgical fastening apparatus. According to one aspect of the present disclosure, the second material is more flexible than the first material. In another aspect of the present disclosure, the proximal portion defines a flange configured to engage tissue.

According to another aspect of the present disclosure, the opening is larger than the aperture. In another aspect of the present disclosure, the distal portion defines a folded configuration. The folded configuration may act as a barrier between the surgical fastening apparatus and a section of tissue.

In another aspect of the present disclosure, the distal portion defines a partially enclosed distal end. The partially enclosed distal end may be reconfigurable upon forced contact with the surgical fastening apparatus.

According to another aspect of the present disclosure, the proximal portion and the distal portion are monolithically formed. In still another aspect of the present disclosure, the proximal portion and the distal portion are releasably coupled.

According to another aspect of the present disclosure, a method of withdrawing a surgical instrument from an access device is disclosed, and includes providing a tubular access device defining a partially enclosed distal end having an aperture. The method also includes inserting a surgical fastening apparatus through the aperture such that the partially enclosed distal end frictionally engages the surgical fastening apparatus. The method also includes withdrawing the surgical fastening apparatus through the access device such that a distal portion of the access device folds radially inward and proximally. In another aspect of the present disclosure, the method includes maintaining a barrier between the surgical access device and a section of tissue via the distal portion of the access device.

BRIEF DESCRIPTION OF THE DRAWINGS

Various embodiments of the presently disclosed surgical stapling device and access device are disclosed herein with reference to the drawings, wherein.

DETAILED DESCRIPTION

With reference now to the drawings wherein like numerals represent like elements throughout the several views, the presently-disclosed surgical fastening apparatus will be described. As used herein, the term "operator" may refer to any user, e.g., a nurse, doctor, or clinician, of the presently-disclosed surgical fastening apparatus. Further, the term "distal" refers to that portion of the surgical fastening apparatus, or component thereof, farther from the operator while the term "proximal" refers to that portion of the surgical fastening apparatus, or component thereof, closer to the operator.

Figure 1:
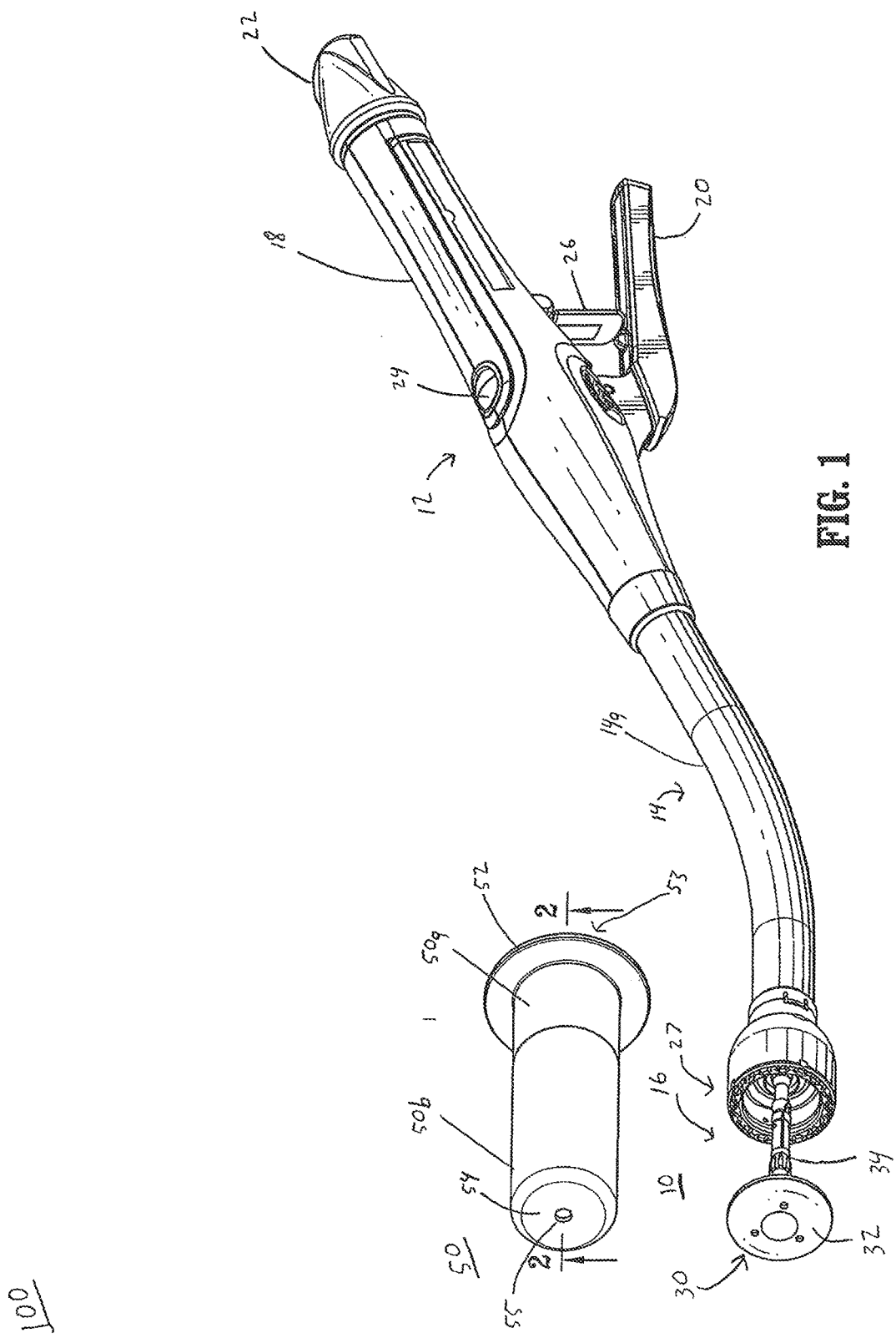
FIG. 1 is a perspective view of a system including a surgical fastening device and an access device.

Referring initially to FIG. 1, an embodiment of the presently disclosed surgical system is illustrated generally as 100. Surgical system 100 includes a surgical fastening apparatus 10 and an access device 50. Access device 50 is configured to provide an entry path for surgical fastening apparatus 10 to a working site within a patient, as will be described further below.

Briefly, surgical fastening apparatus 10 includes a proximal handle assembly 12, an elongated central body portion 14 including a curved elongated outer tube 14a, and a distal head portion 16. Distal head potion 16 includes a shell assembly 27 and an anvil assembly 30, as will be described further below. In some embodiments, the length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 may be formed from separate handle sections (not shown), which together define a housing for the internal components of surgical fastening apparatus 10. A pivotally mounted trigger lock 26 is fastened to handle assembly 12 and is manually positioned to prevent inadvertent firing or actuation of surgical fastening apparatus 10. Indicator 24 is positioned on the stationary handle 18 and includes indicia, e.g., color coding, alpha-numeric labeling, etc., to identify to an operator whether the surgical fastening apparatus 10 has been fired or actuated and/or when the surgical fastening apparatus 10 is ready to be fired.

The surgical device may comprise other types of devices such as clip appliers, electrosurgical instruments, scalpels, ultrasonic instruments, etc. In addition, in any of the embodiments disclosed herein, a surgical stapling instrument can be motorized or otherwise powered. A power source and/or motor can be provided for powering the surgical stapling instrument. The surgical stapling instrument, in any embodiment herein, can be configured to be used with a robotic surgical system. In addition, the surgical stapler can be linear, circular or otherwise configured.

Figure 2:
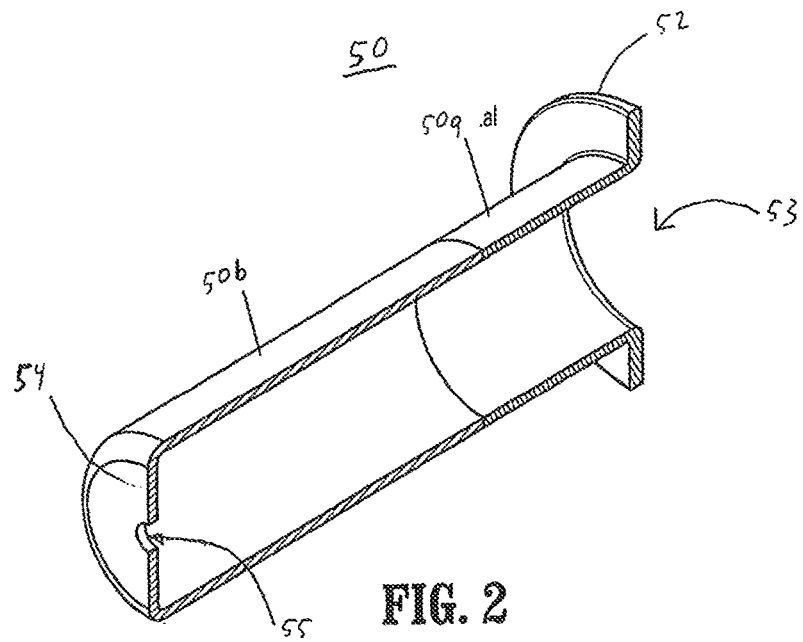
FIG. 2 is a cross-sectional perspective view taken along section line 2-2 of FIG. 1.

With additional reference to FIG. 2, access device 50 is an elongate tubular member having a proximal portion 50a and a distal portion 50b. Access device 50 defines an internal lumen and has a proximal flange 52 circumscribing a proximal opening 53, and a partially enclosed distal end 54 including a distal aperture 55. The distal aperture 55 has a different, i.e., smaller, dimension than the proximal opening 53 such that an object may pass uninhibited through the proximal opening 53, but may encounter resistance at the distal aperture 55, as will be described further below.

Proximal portion 50a and distal portion 50b of access device 50 may be formed of different materials. In some embodiments, distal portion 50b may be formed of a more flexible material than proximal portion 50a of access device 50. Accordingly, proximal portion 50a of access device 50 may be formed of a more rigid material than distal portion 50b of access device 50. In this manner, distal portion 50b of access device 50 may be configured to flex, fold, bend, and/or deform relative to proximal portion 50a of access device 50. Proximal portion 50a of access device 50 may be releasably coupled with distal portion 50b of access device 50, or access device 50 may be monolithically formed. In other embodiments, proximal and distal portions 50a, 50b of access device 50 may be formed of materials with similar or identical material properties.

Figure 3:
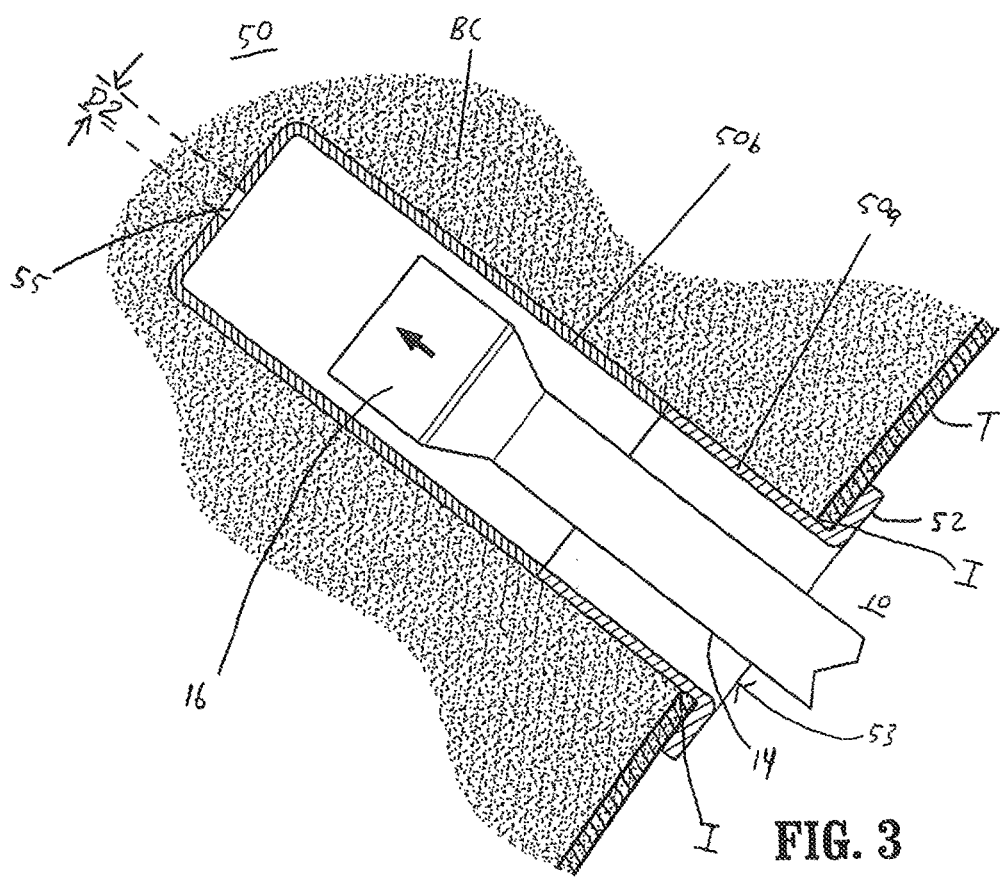
FIG. 3 is a side, cross-sectional view of the access device shown in FIG. 1, inserted into tissue, and with a portion of the surgical fastening device being advanced therealong.

Referring to FIG. 3, access device 50 may be inserted into a layer of tissue "T" and into a body cavity "BC" therebelow to provide access to a working site within a patient, e.g., a target hollow body structure or tubular organ. Access device 50 may be inserted through a naturally-occurring orifice or a pre-formed incision "I" in the layer of tissue "T." Accordingly, access device 50 may be configured to be inserted through the incision "I" in conjunction with a tissue penetrating member, e.g., a trocar or obturator.

Access device 50 is advanced distally into the body cavity "BC" until the flange 52 engages the layer of tissue "T." In this manner, flange 52 abuts the layer of tissue "T" and serves as an anchor to inhibit over-insertion of the access device 50 into the body cavity "BC." Further, the increased cross-sectional area presented by the flange 52 evenly distributes forces generated by movement of the access device 50 during the course of operation across the layer of tissue "T," e.g., to minimize damage to the layer of tissue "T."

A portion of the surgical fastening apparatus 10, i.e., the central body portion 14 and distal head portion 16 are inserted into the proximal opening 53 of the access device 50 and advanced therealong toward the distal portion 50b of the access device 50.

Figure 4:
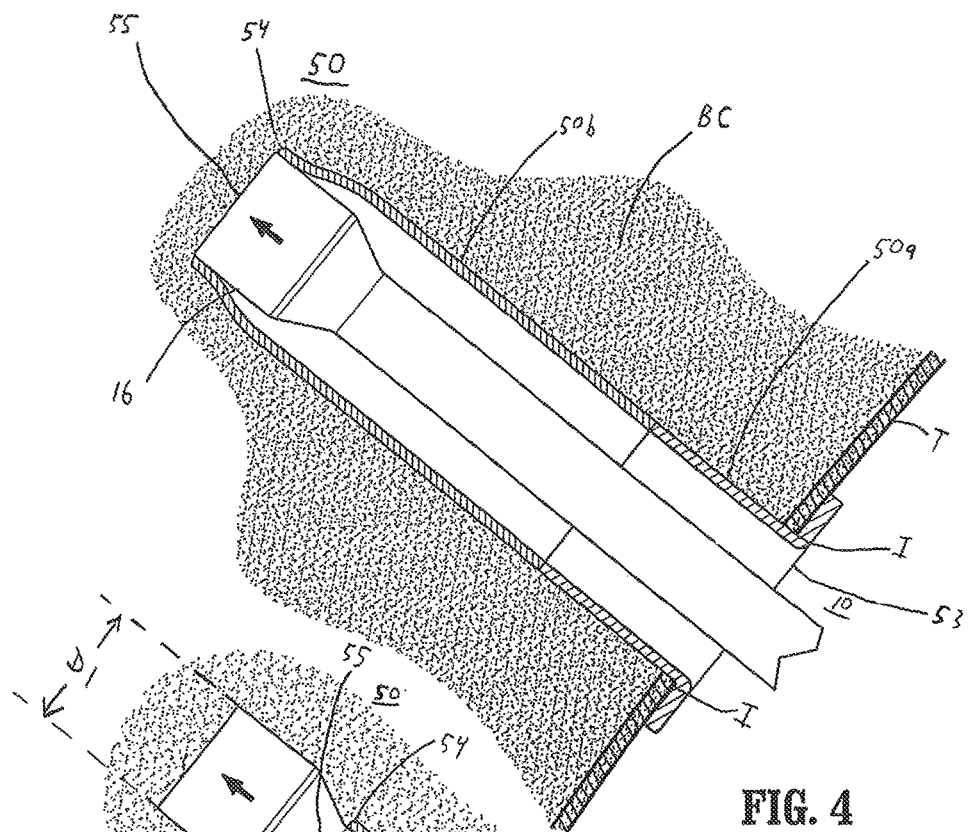
FIG. 4 is a side, cross-sectional view of the access device shown in FIG. 1, inserted into tissue, and with a portion of the surgical fastening device being advanced to contact a distal end of the access device.

Turning to FIG. 4, the distal head portion 16 of the surgical fastening apparatus 10 is shown engaging the partially enclosed distal end 54 of the access device 50. As shown, the distal head 16 of the surgical fastening device 10 defines a cross-sectional diameter "D1" (FIG. 5) that is different, i.e., greater, than an initial or unexpanded cross sectional diameter "D2" (FIG. 3) of the distal aperture 55 of the access device 50. Accordingly, the distal head portion 16 of the surgical fastening apparatus 10 will contact the partially enclosed distal end 54 of the access device 50 before passing through the distal aperture 55 of the access device.

As the distal head portion 16 of the surgical fastening apparatus 10 is advanced further distally through the access device 50, the distal head portion will cause the partially enclosed distal end 54 of access device 50 to deform to accommodate the larger cross-sectional diameter "D2" of the distal head portion 16, i.e., the distal aperture 55 of the access device 50 will dilate to facilitate passage of the distal head portion 16 therethrough. As described above, the distal portion 50*b* of the access device 50 is formed of a material with a greater flexibility than the proximal portion 50*a* of access device 50. Accordingly, the distal portion 50*b* of the access device 50 is pliant upon forced contact with the surgical fastening apparatus 10 by an operator. The passage of the distal head portion 16 of the surgical fastening apparatus 10 through the distal aperture 55 of the access device 50 may exert a frictional resistance such that a tactile indication of the passage of the distal head portion 16 through the distal opening 54 of the access device 50 is provided to an operator.

Figure 5:
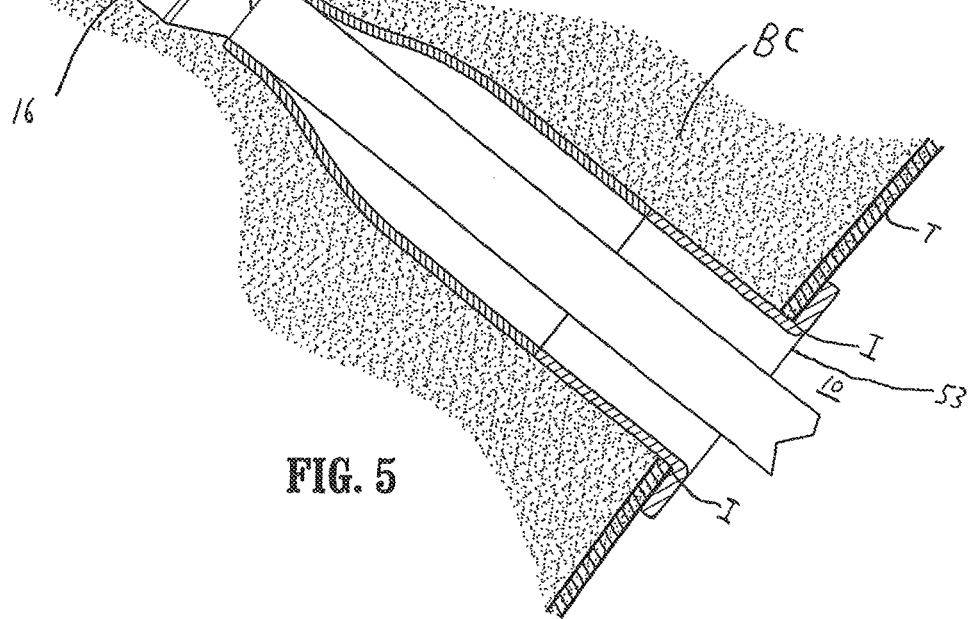
FIG. 5 is a side, cross-sectional view of the access device shown in FIG. 1, inserted into tissue, and with a portion of the surgical fastening device being inserted therethrough.

Turning now to FIG. 5, after passage of the distal head portion 16 of the surgical fastening apparatus 10 through the distal aperture 55 of the access device 50, the partially enclosed distal end 54 of the access device 50 circumscribes and proximally abuts the distal head portion 16 of the surgical fastening apparatus 10. With the distal head portion 16 of the surgical fastening apparatus 10 clear of the access device 50, an operator may begin a minimally invasive procedure, e.g., on hollow body organs or tissue sections within the body cavity "BC."

Briefly, and with additional reference back to FIG. 1, distal head portion 16 of surgical fastening apparatus 10 is positioned to engage adjacent sections of tissue. The distal head portion 16 of surgical fastening apparatus 10 is positioned such that adjacent sections of tissue are disposed between the shell assembly 27 and the anvil head 32, with an anvil center rod assembly 34 extending therebetween. An operator may then rotate approximation knob 22 (FIG. 1) to approximate anvil head 32 toward shell assembly 27. An operator may then engage firing trigger 20 (FIG. 1) to effect one or more firing strokes of surgical fastener apparatus 10. Upon a firing stroke of the surgical fastening apparatus 10, a plurality of fasteners, e.g., staples (not shown), are ejected from shell assembly 27 into the pockets (not shown) of the anvil head 32 to effect joining of tissue. During the course of such a minimally invasive procedure, components of the distal head portion 16 of the surgical fastening apparatus 10 may contact septic and/or diseased, e.g., cancerous, sections of tissue. As the distal head portion 16 may be considered "contaminated" by contact with such materials, it may be desirable to minimize further contact between the distal head portion 16 of the surgical fastening apparatus 10 and the incision "I" or other point of entry of the surgical fastener apparatus 10 into the layer of tissue "T," e.g., to minimize the risk of infection.

Accordingly, upon completion of a minimally invasive surgical procedure with the surgical fastening apparatus 10, an operator may withdraw the surgical fastening apparatus 10 proximally away from the working site through the body cavity "BC." As the distal head portion 16 is frictionally engaged with the distal aperture 55 of the access device 50, the partially enclosed distal end of the access device 50 will be carried with movement of the distal head portion 16. Accordingly, as the surgical fastening apparatus 10 is withdrawn proximally, the distal portion 50*b* of the access device 50 will invert, i.e., fold radially inwardly and proximally, such that the exterior surface of the distal portion 50*b* of the access device 50 is disposed at an interior portion of the access device 50. In this manner, access device 50 is reconfigurable between a first condition, in which the access device 50 is not folded (FIG.3), and a second condition, in which the access device 50 is inverted as described above (FIG.6).

Figure 6:
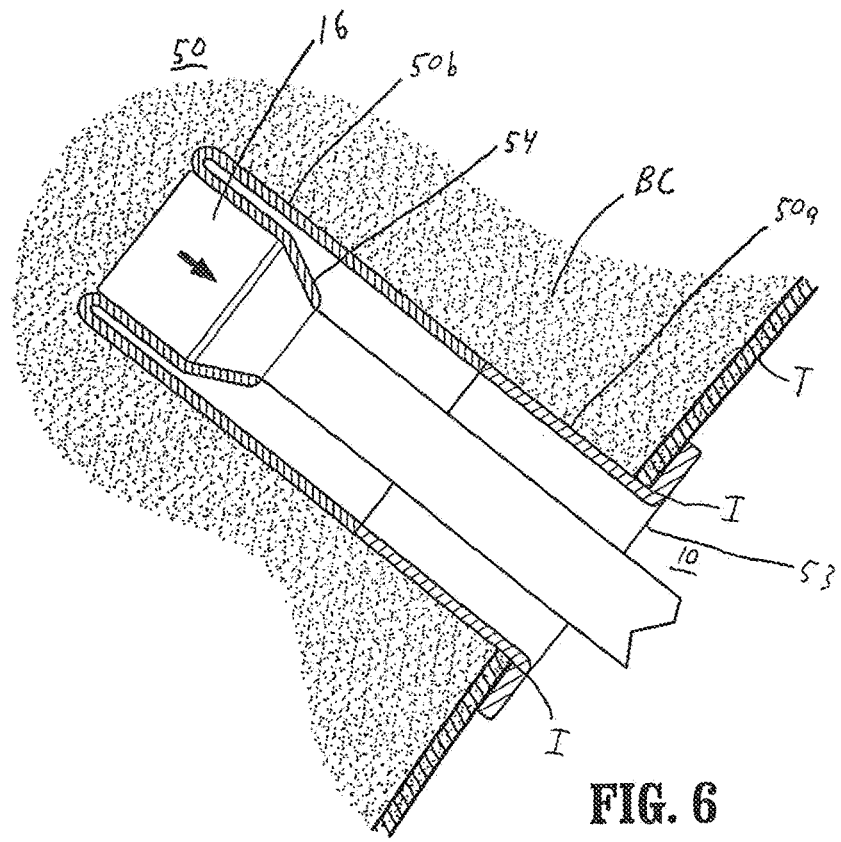
FIG. 6 is a side, cross-sectional view of the access device shown in FIG. 1, inserted into tissue, and with a portion of the surgical fastening device being partially withdrawn therefrom, and with the distal end of the access device being inverted.
Figure 7:
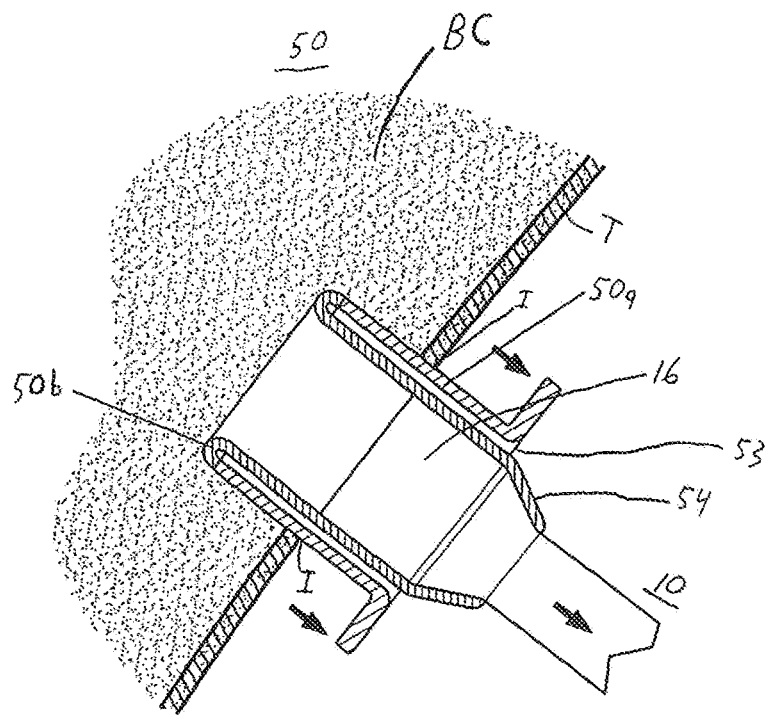
FIG. 7 is a side, cross-sectional view of the access device shown in FIG. 1, inserted into tissue, and with a portion of the surgical fastening device being withdrawn therefrom, the distal end of the access device being withdrawn past a proximal end of the access device.

Referring now to FIGS. 6 and 7, as the surgical fastening apparatus 10 is withdrawn further proximally, the distal head portion 16 carries the partially enclosed distal end 54 of the access device 50 therewith such that the access device 50 further inverts in the manner described above. Accordingly, the distal head portion 16 of surgical fastening apparatus 10 is withdrawn toward the layer of tissue "T" while disposed interiorly of the access device by virtue of the inverted form of the access device 50. In this manner, the folded surfaces of the access device 50 provide a barrier between the distal head portion 16 of the surgical fastening apparatus 10 and the layer of tissue "T" and surrounding tissue structures. This protects against septic or diseased materials being transmitted away from the working site and toward other tissues, such as the incision "I" and layer of tissue "T." In addition, the surrounding tissue is protected from potentially sharp or pinching parts of the surgical instrument.

Because the proximal section 50*a* is formed of a different, e.g., more rigid material than the distal section 50*b* of the access device 50, the inversion of the access device 50 may be limited to the distal section 50*b* of the access device 50, while the proximal portion 50*a* of the access device 50 undergoes minimal if any deformation. In some embodiments, the entire access device 50 may be configured to invert.

The access device 50, with the distal head section 16 of the surgical fastening apparatus 10 engaged therewith, may then be removed from the layer of tissue "T" for sterilization and/or storage, or disposal.

It will be understood that various modifications may be made to the embodiments disclosed herein. Therefore, the above description should not be construed as limiting, but merely as exemplifications of disclosed embodiments. For example, surgical instruments other than the circular stapler shown could be used. Those skilled in the art will envision other modifications within the scope and spirit of the claims appended hereto.

The invention claimed is:

1. A surgical system, comprising:
a surgical fastening apparatus; and
an access device having a distal aperture and a cylindrical portion defining an internal lumen configured to receive the surgical fastening apparatus,
wherein the access device is reconfigurable between a first condition, in which the access device has a maximum length with a distal portion of the surgical fastening apparatus extending through the distal aperture, and a different, second condition in which a distal portion of the access device is radially inverted inwardly into the internal lumen upon proximal movement of the surgical fastening apparatus relative to the access device with the distal portion of the surgical fastener apparatus extending through the distal aperture.

2. The surgical system of claim 1, wherein the access device defines a partially enclosed distal end.

3. The surgical system of claim 1, wherein the surgical fastening apparatus includes a distal head portion defining a first diameter, and the distal aperture defines a second, different diameter.

4. The surgical system of claim 3, wherein the second diameter is smaller than the first diameter.

5. The surgical system of claim 1, wherein a portion of the surgical fastening apparatus is configured to frictionally engage the distal aperture.

6. The surgical system of claim 1, wherein a proximal portion of the access device includes a flange.

7. The surgical system of claim 1, wherein the surgical fastening apparatus is a circular stapler having a head.

\* \* \* \* \*